(12) United States Patent
Ooms et al.

(10) Patent No.: US 8,552,214 B2
(45) Date of Patent: Oct. 8, 2013

(54) PROCESS FOR PREPARING DIALKYL CARBONATES

(75) Inventors: Pieter Ooms, Krefeld (DE); Friedhelm Risse, Köln (DE); Andre Düx, Brühl (DE); Carsten Buchaly, Düsseldorf (DE); Thomas Pancur, Altenholz (DE); Arthur Susanto, Köln (DE); Georg Ronge, Düsseldorf (DE); Johan Vanden Eynde, Zwijnaarde (BE); Wim Wuytack, Zele (BE)

(73) Assignee: Bayer MaterialScience AG (DE)

( * ) Notice: Subject to any disclaimer, the term of this patent is extended or adjusted under 35 U.S.C. 154(b) by 69 days.

(21) Appl. No.: 13/018,592

(22) Filed: Feb. 1, 2011

(65) Prior Publication Data
US 2011/0237819 A1 Sep. 29, 2011

(30) Foreign Application Priority Data
Feb. 3, 2010 (DE) .................... 10 2010 006 657

(51) Int. Cl.
*C07C 69/96* (2006.01)
(52) U.S. Cl.
USPC ........................................................ 558/277
(58) Field of Classification Search
USPC ........................................................ 558/277
See application file for complete search history.

(56) References Cited

U.S. PATENT DOCUMENTS

| | | | |
|---|---|---|---|
| 3,642,858 A | 2/1972 | Frevel et al. | |
| 3,803,201 A | 4/1974 | Gilpin et al. | |
| 4,062,884 A | 12/1977 | Romano et al. | |
| 4,162,200 A | 7/1979 | Himmele et al. | |
| 4,181,676 A | 1/1980 | Buysch et al. | |
| 4,307,032 A | 12/1981 | Krimm et al. | |
| 4,661,609 A | 4/1987 | Knifton | |
| 4,691,041 A | 9/1987 | Duranleau et al. | |
| 4,734,519 A | 3/1988 | Dunski et al. | |
| 5,231,212 A | 7/1993 | Buysch et al. | |
| 5,344,954 A * | 9/1994 | Schon et al. | 558/274 |
| 5,359,118 A | 10/1994 | Wagner et al. | |
| 5,360,923 A | 11/1994 | Nickel et al. | |
| 6,930,195 B2 | 8/2005 | Buchanan et al. | |
| 2003/0023109 A1 | 1/2003 | Schlosberg et al. | |
| 2007/0197816 A1 | 8/2007 | Van Der Heide et al. | |

FOREIGN PATENT DOCUMENTS

| | | |
|---|---|---|
| EP | 0001082 A1 | 3/1979 |
| EP | 0001083 A1 | 3/1979 |
| EP | 0180387 A2 | 5/1986 |
| EP | 0298167 A1 | 1/1989 |
| EP | 530615 A2 | 3/1993 |
| EP | 0569812 A1 | 11/1993 |
| EP | 581115 A2 | 2/1994 |
| EP | 592883 A1 | 4/1994 |
| EP | 1086940 A1 | 3/2001 |
| EP | 1927583 B1 | 5/2012 |
| JP | 2003-104937 A | 4/2003 |
| WO | WO-2007/096340 A1 | 8/2007 |
| WO | WO-2007/096343 A1 | 8/2007 |

OTHER PUBLICATIONS

European Patent Office Search Report for EP 11 15 2683 (Aug. 17, 2012)

* cited by examiner

*Primary Examiner* — Samantha Shterengarts
(74) *Attorney, Agent, or Firm* — Novak Druce Connolly Bove + Quigg LLP

(57) ABSTRACT

The present invention relates to a continuous process for preparing lower dialkyl carbonates as main product and alkylene glycol as by-product by transesterification of a cyclic alkylene carbonate (e.g. ethylene carbonate or propylene carbonate) with lower alkyl alcohols in the presence of a catalyst and also the required purification of the dialkyl carbonate in a subsequent process step. To optimize the economics and energy efficiency of the process, additional devices are used for intermediate heating of the liquid streams in the apparatus.

6 Claims, 6 Drawing Sheets

PROCESS FOR PREPARING DIALKYL CARBONATES

RELATED APPLICATIONS

This application claims benefit to German Patent Application No. 10 2010 006 657.5, filed Feb. 3, 2010, which is incorporated herein by reference in its entirety for all useful purposes.

BACKGROUND OF THE INVENTION

The present invention relates to a continuous process for preparing lower dialkyl carbonates as main product and alkylene glycol as by-product by transesterification of a cyclic alkylene carbonate (e.g. ethylene carbonate or propylene carbonate) with lower alkyl alcohols in the presence of a catalyst and also the required purification of the dialkyl carbonate in a subsequent process step. To optimize the economics and energy efficiency of the process, additional devices are used for intermediate heating of the liquid streams in the apparatus.

The preparation of dialkyl carbonates from cyclic alkylene carbonate and alkyl alcohol, in which alkylene glycol is simultaneously formed as by-product, is known and has been widely described. In U.S. Pat. No. 6,930,195 B, this catalysed transesterification reaction has been described as a two-stage equilibrium reaction. In the first reaction stage, the cyclic alkylene carbonate reacts with alkyl alcohol to form hydroxyalkyl carbonate as intermediate. The intermediate is then converted by means of alkyl alcohol in the second reaction stage into the products: dialkyl carbonate and alkylene glycol.

For the industrial implementation of the dialkyl carbonate production process, the use of a reactive distillation column (also referred to below as transesterification column), which has been described, inter alia, in EP 530 615 A, EP 569 812 A and EP 1 086 940 A, has been found to be particularly advantageous. In EP 569 812 A, the cyclic alkylene carbonate is fed continuously into the upper part of the transesterification column and the alkyl alcohol containing dialkyl carbonate is fed continuously into the middle or lower part of the transesterification column. In addition, virtually pure alkyl alcohol is introduced below the point of introduction of the alkyl alcohol containing dialkyl carbonate. According to the present invention a substance is referred to as being virtually pure, if the content of impurities is less than 2% by weight, preferably less than 1% by weight. The high boiler mixture which comprises the alkylene glycol produced as a by-product is taken off continuously at the bottom of the transesterification column. The low boiler mixture, which comprises the dialkyl carbonate produced, is taken off at the top of the transesterification column as the dialkyl carbonate/alkyl alcohol mixture and subjected to a further purification step.

The distillation column for purifying the dialkyl carbonate/alkyl alcohol mixture is operated at a higher pressure than that prevailing in the transesterification column, so that a further dialkyl carbonate/alkyl alcohol mixture having a lower dialkyl carbonate content can be taken off at the top of this distillation column. The dialkyl carbonate as main product is obtained in high purity at the bottom of this purification column.

Many factors play an important role in the development of an economically attractive process for preparing dialkyl carbonates. Most literature references are concerned with the reaction parameters such as conversion, selectivity or product purity. The energy efficiency of the process is more rarely addressed (e.g. in EP 569 812 A, JP2003-104937, WO 2007/096340, WO 2007/096343), even though this factor makes a not inconsiderable contribution to the economic attractiveness of the process. In the present invention, measures for increasing the energy efficiency of the process are therefore introduced.

In EP 569 812 A, the energy input in the preparation of the dialkyl carbonate is reduced by many streams in the process not being condensed but being conveyed as gaseous streams.

WO 2007/096340 describes a process in which alkylene carbonate is produced from alkylene oxide and $CO_2$ and the alkylene carbonate is subsequently reacted with alkyl alcohol to form dialkyl carbonate and alkylene glycol, with the mixture formed in the second step, which contains dialkyl carbonate and alkylene glycol, being purified. The reaction to form the alkylene carbonate is exothermic and the corresponding alkylene carbonate product stream is used to heat the dialkyl carbonate/alkylene glycol product stream in the purification.

In WO 2007/096343, the mixture of dialkyl carbonate and alkyl alcohol formed from alkylene carbonate and alkyl alcohol in a transesterification column is purified by means of extractive distillation, with alkylene carbonate serving as extractant. After the dialkyl carbonate has been separated from the extractant by distillation, the hot bottoms from this column, which contain the extractant, is used to heat the alkyl alcohol fed to the transesterification column.

JP 2003-104937 looks at various process variants for working up an ethylene carbonate/ethylene glycol mixture and providing the purified ethylene carbonate for the process for preparing dimethyl carbonate from the point of view of energy consumption, too.

However, none of the abovementioned documents describes processes or procedures by means of which the reaction of alkylene carbonate with alkyl alcohol in the transesterification column can be carried out particularly energy-efficiently while maintaining the quality of the main product (dialkyl carbonate) and of the by-product (alkylene glycol). For this reason, measures for increasing the energy efficiency in this process step are introduced in the present invention.

There was therefore a need for a process which has a higher energy efficiency in the transesterification column while maintaining the same quality of the dialkyl carbonate and the alkylene glycol.

BRIEF DESCRIPTION OF THE INVENTION

An embodiment of the present invention is a process for preparing dialkyl carbonate from cyclic alkylene carbonate and alkyl alcohol in at least one transesterification column, and at least one subsequent distillation column for purifying the dialkyl carbonate formed in the transesterification column, wherein the transesterification column comprises at least one reaction zone, at least one enrichment section arranged above the reaction zone, the column containing at least one enrichment section in the upper part of the column and at least one stripping section in the lower part of the column, wherein the process further comprises heating a liquid stream in the at least one transesterification column and/or vaporizing, entirely or partly, one of the dialkyl carbonate-containing alkyl alcohol streams fed to the at least one transesterification column with a technical device, wherein the temperature $T_I$ of a medium for heating the internal liquid stream in the column and/or for vaporizing an introduced dialkyl carbonate-containing alkyl alcohol stream is less than a temperature $T_{BV}$ of a medium used in a bottom vaporizer, recovering, either partly or entirely, the energy of the medium for heating the internal liquid stream in the column and/or for vaporizing an introduced dialkyl carbonate-containing alkyl alcohol stream in another chemical production process, and wherein with the proviso that a liquid stream is heated in the transesterification column, the technical device for heating the liquid stream is arranged above a bottom vaporizer of the at least one transesterification column.

Another embodiment of the present invention is the above process, wherein the energy at the temperature level $T_I$ is made available, in its entirety or in part, directly or indirectly by condensation as heat of condensation.

Another embodiment of the present invention is the above process, wherein the at least one transesterification column comprises a stripping section arranged below the reaction zone.

Another embodiment of the present invention is the above process, wherein the technical device for heating the internal liquid stream in the column is arranged in the stripping section.

Another embodiment of the present invention is the above process, wherein the technical device for heating the internal liquid stream in the column is positioned within or outside the transesterification column.

Another embodiment of the present invention is the above process, wherein the transesterification is carried out in countercurrent in at least one transesterification column in the presence of a catalyst in such a way that alkylene carbonate is introduced into the upper part of the column and a dialkyl carbonate-containing alkyl alcohol having a dialkyl carbonate content of from 0.2 to 30% by weight is introduced into the middle or lower part of the reaction zone of the at least one transesterification column.

Another embodiment of the present invention is the above process, wherein a further stream comprising virtually pure alkyl alcohol is fed into the at least one transesterification column at a point of introduction arranged below the point of introduction of the dialkyl carbonate-containing alkyl alcohol stream.

Another embodiment of the present invention is the above process, wherein the energy of the medium is recovered at the temperature level $T_I$ in the condensation of the mixture at the top of the at least one distillation column for purifying the dialkyl carbonate.

DETAILED DESCRIPTION OF THE INVENTION

Figure 1:
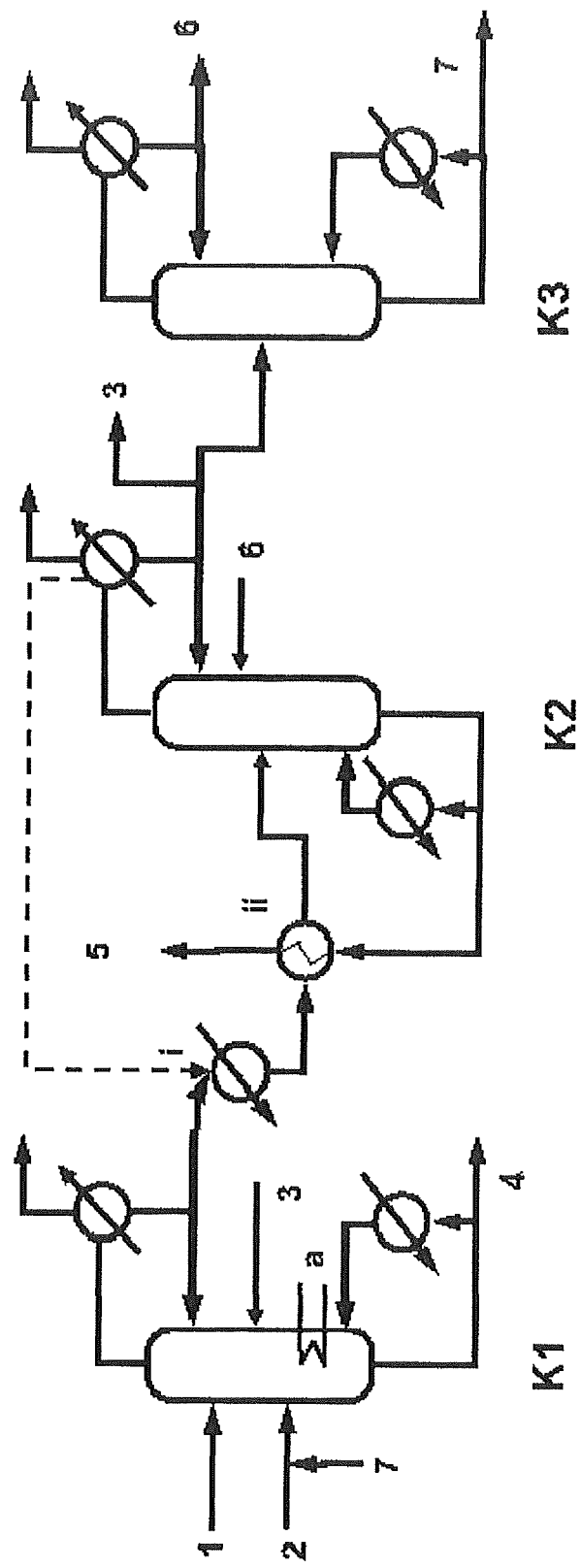
FIG. 1 depicts a process for preparing dialkyl carbonates according to an embodiment of the present invention.

It has now been discovered that, to increase the energy efficiency, the quantity of heat energy at the temperature level $T_{BV}$ required for operating the bottom vaporizer of the transesterification column can be reduced particularly simply and advantageously while maintaining the same product quality by using an additional technical device for intermediate heating in the transesterification column, with the heat of condensation liberated in the overhead condenser or the heat from the bottoms from the dialkyl carbonate purification column being recovered and used either directly or indirectly, in its entirety or in part for intermediate heating.

Due to the lower temperature of the internal stream of the transesterification column compared to the temperature at the bottom of this column, heat energy at the temperature level $T_I$, where $T_I < T_{BV}$, can be used for intermediate heating. This concept leads overall to a reduction in the consumption of heat energy at a temperature level greater than or equal to $T_{BV}$ because the heat energy obtained at a temperature level below $T_{BV}$ in a condensation or in the cooling of a stream which can also originate from other chemical production processes can now be utilized in a useful way and the amount of generally more costly heat energy at a temperature level greater than or equal to $T_{BV}$ can be reduced.

Low-grade steam can be obtained from the heat of condensation liberated at the overhead condenser of the dialkyl carbonate purification column. It has now been found that this low-grade steam is suitable, for example, for preheating the feed to the dialkyl carbonate purification column, for vaporizing the dialkyl carbonate-containing alkyl alcohol stream to the transesterification column or for intermediate heating of the internal liquid stream in the transesterification column, or for realizing a combination of the possibilities mentioned.

The heat energy obtained at the overhead condenser or from the bottoms from the dialkyl carbonate purification column or the heat energy at the temperature level $T_I$ obtained in other chemical production processes can be supplied either directly or indirectly to the intermediate heater. In the case of direct supply, the stream which is to be condensed or cooled heats the internal stream of the transesterification column by means of the intermediate heater. In the case of indirect supply, the stream to be condensed or cooled heats the stream in the column via the intermediary of one or more heat transfer media. Possible heat transfer media are gases, vapours or liquids, preferably gaseous or liquid industrial heat transfer media such as water, heat transfer media based on mineral oil or synthetic heat transfer media (e.g. Diphyl™, Marlotherm®). Particularly preferred heat transfer media are water and steam.

Furthermore, it has surprisingly been found that in the case of intermediate heating in the transesterification column, this can preferably be positioned between the bottom of the column and the lowermost inlet for reactants. In this way, the proportion by weight of unreacted alkylene carbonate in the bottom product from the transesterification column can continue to be kept below 1000 ppm, preferably below 500 ppm. The low-grade steam for the intermediate heater is, as mentioned above, generated at the overhead condenser of the dialkyl carbonate purification column.

The intermediate heater can be integrated into the transesterification column or be configured as a separate intermediate heater outside the column. The internal or external intermediate heater can have one or more stages (i.e. one or more heat exchangers). In addition, the intermediate heater can, according to the invention, have various possible constructions, e.g. integrated heating matrices or heating coils in the case of an internal embodiment and, for example, plate heat exchangers or shell-and-tube heat exchangers in the case of an external embodiment. Such constructions are known to those skilled in the art.

In the preferred internal embodiment, the intermediate heater of the distillation column for purifying the dialkyl carbonate preferably has a length of from 100 to 10 000 mm and the ratio of the diameter of the intermediate heater to the column diameter is preferably from 0.1 to 1. Furthermore, the intermediate heater preferably has a heat transfer area of from 1 to 5000 m².

The vaporization of the dialkyl carbonate-containing alkyl alcohol stream can be carried out in one or more stages by means of heat exchangers such as plate heat exchangers or shell-and-tube heat exchangers.

Due to the reduction of the consumption of heat energy at the high temperature level $T_{BV}$ with simultaneous maintenance of the high product quality, the process of the invention gives a significant economic advantage.

Dialkyl carbonates purified according to the invention are preferably those of the general formula (I)

(I)

where $R^1$ and $R^2$ are each, independently of one another, linear or branched, optionally substituted $C_1$-$C_{34}$-alkyl, preferably $C_1$-$C_6$-alkyl, particularly preferably $C_1$-$C_4$-alkyl. $R^1$ and $R^2$ can be identical or different. Preference is given to $R^1$ and $R^2$ being identical.

For the purposes of the invention, $C_1$-$C_4$-alkyl is, for example, methyl, ethyl, n-propyl, isopropyl, n-butyl, sec-butyl, tert-butyl, $C_1$-$C_6$-alkyl also, for example, n-pentyl, 1-methylbutyl, 2-methylbutyl, 3-methylbutyl, neopentyl, 1-ethylpropyl, cyclohexyl, cyclopentyl, n-hexyl, 1,1-dimethylpropyl, 1,2-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl or 1-ethyl-2-methylpropyl, $C_1$-$C_{34}$-alkyl also, for example, n-heptyl and n-octyl, pinacyl, adamantyl, the isomeric menthyls, n-nonyl, n-decyl, n-dodecyl, n-tridecyl, n-tetradecyl, n-hexadecyl or n-octadecyl. The same applies to the corresponding alkyl radical in, for example, aralkyl or alkylaryl radicals. Alkylene radicals in the corresponding hydroxyalkyl or aralkyl or alkylaryl radicals are, for example, the alkylene radicals corresponding to the above alkyl radicals.

The above listings are to be understood as being by way of example and not constituting a limitation.

Preferred dialkyl carbonates are dimethyl carbonate, diethyl carbonate, di(n-propyl) carbonate, di(iso-propyl) carbonate, di(n-butyl) carbonate, di(sec-butyl) carbonate, di(tert-butyl) carbonate and dihexyl carbonate. Particular preferences is given to dimethyl carbonate and diethyl carbonate. Very particular preference is given to dimethyl carbonate.

The dialkyl carbonates are preferably prepared from cyclic alkylene carbonates having the formula (II):

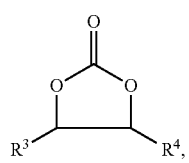
(II)

where, in the formula, $R^3$ and $R^4$ are each, independently of one another, hydrogen, substituted or unsubstituted $C_1$-$C_4$-alkyl, substituted or unsubstituted $C_2$-$C_4$-alkenyl or substituted or unsubstituted $C_6$-$C_{12}$-aryl and $R^3$ and $R^4$ together with the two three-ring carbon atoms can form a saturated carbocyclic ring having 5-8 ring atoms.

The cyclic alkylene carbonates are reacted with alcohols of the formula

where $R^5$ is a straight-chain or branched $C_1$-$C_4$-alkyl.

Transesterification catalysts used to produce the dialkyl carbonates are those known to a person skilled in the art, for example hydrides, oxides, hydroxides, alkoxides, amides or salts of alkali metals such as lithium, sodium, potassium, rubidium and caesium, preferably of lithium, sodium and potassium, particularly preferably of sodium and potassium (U.S. Pat. No. 3,642,858 A, U.S. Pat. No. 3,803,201 A, EP 1 082 A). If alkoxides are used, these can also be formed in situ by use of the elemental alkali metals and the alcohol to be reacted. Salts of alkali metals can be those of organic or inorganic acids, e.g. of acetic acid, propionic acid, butyric acid, benzoic acid, stearic acid, carbonic acid (carbonates or hydrogencarbonates), of hydrochloric acid, hydrobromic acid or hydroiodic acid, nitric acid, sulphuric acid, hydrofluoric acid, phosphoric acid, hydrocyanic acid, thiocyanic acid, boric acid, stannic acid, $C_1$-$C_4$-stannonic acids or antimonic acids. As compounds of alkali metals, preference is given to the oxides, hydroxides, alkoxides, acetates, propionates, benzoates, carbonates and hydrogencarbonates, with particular preference being given to using hydroxides, alkoxides, acetates, benzoates or carbonates. Such alkali metal compounds (if appropriate formed in situ from the free alkali metals) are used in amounts of from 0.001 to 2% by weight, preferably from 0.003 to 1.0% by weight, particularly preferably from 0.005 to 1.0% by weight, based on the reaction mixture to be reacted.

It is possible, if appropriate, to add complexing substances to such alkali metal compounds. Examples which may be mentioned are crown ethers such as dibenzo-18-crown-6, polyethylene glycols or bicyclic nitrogen-containing cryptands.

Such complexing agents are used in amounts of from 0.1 to 200 mol %, preferably from 1 to 100 mol %, based on the alkali metal compound.

Further suitable catalysts for the preparation of dialkyl carbonates are thallium(I) and thallium(III) compounds such as the oxides, hydroxides, carbonates, acetates, bromides, chlorides, fluorides, formates, nitrates, cyanates, stearates, naphthenates, benzoates, cyclohexylphosphonates, hexahydrobenzoates, cyclopentandienylthallium, thallium methoxide, thallium ethoxide, preferably Tl(I) oxide, Tl(I) hydroxide, Tl(I) carbonate, Tl(I) acetate, Tl(III) acetate, Tl(I) fluoride, Tl(I) formate, Tl(I) nitrate, Tl(I) naphthenate and Tl-(I) methoxide (EP 1 083). The amounts of thallium catalyst are not particularly critical. They are generally 0.0001-10% by weight, preferably 0.001-1% by weight, based on the total reaction mixture. Nitrogen-containing bases can also be used as catalysts (U.S. Pat. No. 4,062,884) in the preparative process. Mention may be made by way of example of secondary or tertiary amines such as triethylamine, tributylamine, methyldibenzylamine, dimethylcyclohexylamine, etc.

The amounts used of the nitrogen-containing bases are from 0.01 to 10% by weight, preferably from 0.1 to 5% by weight, particularly preferably from 0.1 to 1% by weight, based on the total reaction mixture. Compounds from the group consisting of phosphines, stibines, arsines and divalent sulphur and selenium compounds and also their onium salts can also be used as catalysts (EP 180 387, U.S. Pat. No. 4,734,519).

Mention may be made by way of example of the following: tributylphosphine, triphenylphosphine, diphenylphosphine, 1,3-bis(diphenylphosphino)propane, triphenylarsine, trimethylarsine, tributylarsine, 1,2-bis(diphenylarsino)ethane, triphenylantimony, diphenyl sulphide, diphenyl disulphide, diphenyl selenide, tetraphenylphosphonium halide (Cl, Br, I), tetraphenylarsonium halide (Cl, Br, I), triphenylsulphonium halide (Cl, Br), etc.

The preferred amounts used in the case of this group of catalysts are in the range from 0.1 to 10% by weight, preferably from 0.1 to 5% by weight, particularly preferably in the range from 0.1 to 2% by weight, based on the total reaction mixture.

Furthermore, compounds of tin, titanium or zirconium (U.S. Pat. No. 4,661,609 A) can be used as catalysts. Examples of such systems are butylstannonic acid, tin methoxide, dimethyltin, dibutyltin oxide, dibutyltin dilaurate, tributyltin hydride, tributyltin chloride, tin(II) ethylhexanoate, zirconium alkoxides (methyl, ethyl, butyl), zirconium (IV) halides (F, Cl, Br, I), zirconium nitrates, zirconium acetylacetonate, titanium alkoxides (methyl, ethyl, isopropyl), titanium acetate, titanium acetylacetonate, etc.

The amounts of these catalysts which can preferably be used are from 0.1 to 10% by weight, preferably from 0.1 to 5% by weight, based on the total mixture.

It is also possible to use bifunctional catalysts of the formula (III)

in the preparative process. In these bifunctional catalysts, the molar ratio of the two components in square brackets is expressed by the indices m and n. These indices can, independently of one another, assume values of 0.001-1, preferably 0.01-1, particularly preferably 0.05-1 and very particularly preferably 0.1-1. Within the square brackets are uncharged salts in each case composed of a cation and an anion. The indices a and b are, independently of one another, integers of 1-5; the indices c and d are, independently of one another, integers of 1-3, matching the requirements of the valencies of the cations and anions to form such uncharged salts. Furthermore, in (III), A is the cation of a metal belonging to the third period and group IIa, the fourth period and group IIa, IVa-VIIIa, Ib or IIb, the fifth period and group IIa, IVa-VIIa or IVb or the sixth period and group IIa-VIa of the Periodic Table of the Elements in the short period form.

Possible metals for the cation A are taken by a person skilled in the art from the usual depictions of the Periodic Table of the Elements (Mendeleev) in the short period form. A is preferably the cation of one of the metals Mg, Ca, Sr, Ba, Zn, Cu, Mn, Co, Ni, Fe, Cr, Mo, W, Ti, Zr, Sn, Hf, V and Ta, preferably the cation of one of the metals Mg, Ca, Zn, Co, Ni, Mn, Cu and Sn. Apart from the uncomplexed cations of the metals mentioned, cationic oxo complexes of the metals mentioned are also possible, for example titanyl $TiO^{++}$ and chromyl $CrO_2^{++}$.

The anion X associated with the cation A is that of an inorganic or organic acid. Such an inorganic or organic acid can be monobasic or dibasic or tribasic. Such acids and their anions are known to those skilled in the art. Examples of anions of monobasic inorganic or organic acids are: fluoride, bromide, chloride, iodide, nitrate, the anion of an alkanecarboxylic acid having 1-18 carbon atoms and benzoate; examples of anions of dibasic inorganic or organic acids are: sulphate, oxalate, succinate, fumarate, maleate, phthalate and others; examples of tribasic inorganic or organic anions are: phosphate and citrate. Preferred anions X in the catalyst of the formula (III) are: fluoride, chloride, bromide, iodide, sulphate, nitrate, phosphate, formate, acetate, propionate, oxalate, butyrate, citrate, succinate, fumarate, maleate, benzoate, phthalate, decanoate, stearate, palmitate and laurate. Particularly preferred anions X are: chloride, bromide, iodide, acetate, laurate, stearate, palmitate, decanoate, nitrate and sulphate.

As cation B in the catalyst of the formula (III), it is possible to use a cation from the group consisting of alkali or alkaline earth metal cations, quaternary ammonium, phosphonium, arsonium or stibonium cations and ternary sulphonium cations.

As alkali or alkaline earth metal cations, mention may here be made of: the lithium, sodium, potassium, rubidium, caesium, magnesium, calcium, strontium and barium cations, preferably the alkali metal cations mentioned, particularly preferably the sodium cation and the potassium cation.

As cations B, preference is given to those of the formula (IV)

where $Q^1$ is N, P, As or Sb and $R^6$, $R^7$, $R^8$ and $R^9$ are each, independently of one another, straight-chain or branched $C_1$-$C_{18}$ or $C_7$-$C_{12}$-aralkyl and one of the radicals $R^6$-$R^9$ can also be $C_6$-$C_{12}$. B is particularly preferably a cation of the formula (V)

where, $Q^2$ is N or P, preferably N.

In the formulae (IV) and (V), the radicals $R^6$, $R^7$, $R^8$ and $R^9$ are very particularly preferably replaced by the radicals $R^{16}$, $R^{17}$, $R^{18}$ and $R^{19}$ which are each, independently of one another, straight-chain or branched $C_1$-$C_{18}$-alkyl or $C_7$-$C_8$-aralkyl and one of the radicals $R^{16}$ to $R^{19}$ can also be phenyl. The radicals $R^{16}$, $R^{17}$, $R^{18}$ and $R^{19}$ are very particularly preferably replaced by the radicals $R^{26}$, $R^{27}$, $R^{28}$ and $R^{29}$ which are each, independently of one another, $C_1$-$C_8$-alkyl or benzyl and one of the radicals $R^{26}$ to $R^{29}$ can also be phenyl.

Straight-chain or branched $C_1$-$C_{18}$-alkyl is, for example, methyl, ethyl, propyl, isopropyl, butyl, isobutyl, hexyl, octyl, dodecyl, hexadecyl or octadecyl. Preferred alkyl has 1-12 carbon atoms, and particularly preferred alkyl has 1-8 carbon atoms.

$C_7$-$C_{12}$-Aralkyl is, for example, benzyl, phenylethyl, phenylpropyl, naphthylmethyl or naphthylethyl; a preferred aralkyl is benzyl or phenylethyl, very particularly preferably benzyl.

$C_6$-$C_{12}$-Aryl is, for example, phenyl, naphthyl or biphenylyl, preferably phenyl.

The anion Y in the catalyst of the formula (III) is a halide ion such as fluoride, chloride, bromide or iodide, preferably bromide or iodide, particularly preferably iodide. However, it can also have the meaning of other anions mentioned under X if in the specific case the anion X is bromide or iodide.

The bifunctional catalyst of the formula (III) is used in an amount of 0.005-5% by weight, preferably 0.01-3% by weight, particularly preferably 0.01-1% by weight, based on the total transesterification mixture.

Such catalysts can be introduced in homogeneously dissolved form at the top of the column, with alkylene carbonate, alkylene glycol, alcohol or dialkyl carbonate, i.e. solvents intrinsic to the system, being employed as solvents. It is of course also possible to use insoluble transesterification catalysts which are arranged on intermediate trays or in the middle of packing elements. In such a case, introduction of a dissolved catalyst via (2) can be omitted. Suitable heterogeneous catalysts are, for example:

Ion-exchange resins having functional groups selected from among tertiary amines, quaternary ammonium groups, with hydroxide, chloride or hydrogen sulphates being mentioned by way of example as counterions, sulphonic acid groups or carboxyl groups, with hydrogen, alkali metals or alkaline earth metals being mentioned by way of example as counterions for both. These functional groups can be bound either directly or via inert chains to the polymer (U.S. Pat. No. 4,062,884 A, U.S. Pat. No. 4,691,041 A, EP 298 167 A). Mention may also be made of alkali metal or alkaline earth metal silicates impregnated on silicon dioxide supports, and also ammonium-exchanged zeolites.

The preparative process can be carried out continuously or batchwise. Preference is given to a continuous process.

In the process, the cyclic alkylene carbonate compound(s) and the alkyl alcohol(s) are preferably used in a molar ratio of from 1:0.1 to 1:40, particularly preferably from 1:1.0 to 1:30, very particularly preferably from 1:2.0 to 1:20. The molar ratio indicated does not take into account the recirculation of cyclic alkylene carbonate compound or alkyl alcohol into the transesterification column via one or more condenser(s) at the top or one or more bottom vaporizer(s) which may be present.

The catalyst is preferably introduced into the transesterification column together with the stream containing the cyclic alkylene carbonate in dissolved or suspended form via a point of introduction which is arranged above the point of introduction of the alkyl alcohol. As an alternative, the catalyst can also be introduced separately, for example as a solution in the alkyl alcohol, in the alkylene glycol or in a suitable inert solvent. If heterogeneous catalysts are used, these can be used in admixture with the abovementioned packing elements, in suitable form instead of packing elements or as a bed on any built-in column trays.

The transformation from alkylene carbonate and alkyl alcohol to dialkyl carbonate and alkylene glycol is almost entirely carried out in a transesterification column. In preferred embodiments of the process for preparing dialkyl carbonate, the liquid stream taken off at the bottom of this transesterification column can, if appropriate after being concentrated, be subjected to further reaction and/or purification in one or more further steps. Individual steps among such further steps or all such further steps can preferably be carried out in one or more further columns.

Possible transesterification columns or, if appropriate, second or further column(s) are the columns known to those skilled in the art. These are, for example, distillation or rectification columns, preferably reactive distillation or reactive rectification columns.

A suitable column design of the distillation and/or reaction columns used in the process, which encompasses both the determination of the column height, of the column diameter, the selection of column internals and also the dimensioning of the feed and offtake lines, is known to those skilled in the art and may be found in the relevant literature (e.g. Distillation Design, Henry Z. Kister, Mc Graw Hill; Distillation Operation, Henry Z. Kister, Mc Graw Hill; Perry's Chemical Engineering Handbook; Perry & Green).

As regards the condensation in the overhead condenser, various embodiments are conceivable. Suitable overhead condensers are, for example, shell-and-tube heat exchangers or plate heat exchangers. The ratio $d_1/D_1$ of the diameter of the vapour line from the column to the condenser $(d_1)$ to the column diameter of the distillation column $(D_1)$ is preferably in the range from 0.2 to 1.0, particularly preferably in the range from 0.5 to 1. In a particularly preferred embodiment, the overhead condenser can be integrated into the distillation column, so that no vapour line is required between distillation column and overhead condenser. The ratio $d_1/D_1$ is in this case 1. The column cross section after entry into the overhead condenser can, if appropriate, also be matched to the progress of the condensation.

In the case of some forms of condenser, it can be advantageous for the column cross section to be variable. If the vapour to be condensed is, for example, conveyed from the bottom upwards, the amount of vapour decreases in the upwards direction. If the column diameter is reduced in the direction of the top of the column, the column cross section available for the vapour is matched to the amount of vapour which decreases in the upwards direction. Here, the uncondensed vapour does not necessarily have to be taken off at the top. If, for example, a construction in which a plate heat exchanger or shell-and-tube heat exchanger is inserted into the column from the top, the uncondensed vapour can also be taken off at the side.

The transesterification column preferably contains at least one enrichment section in the upper part of the column and at least one reaction zone below the enrichment section. The enrichment section independently has from 0 to 30, preferably from 0.1 to 30, theoretical plates.

In preferred embodiments, the transesterification column has at least one stripping section having from >0 to 20, preferably from 1 to 10 theoretical plates, below a reaction zone.

Furthermore, the transesterification column can preferably be equipped with one or more bottom vaporizer(s). When the transesterification column has a stripping section, preference is given to using an additional bottom vaporizer which completely or partly vaporizes the liquid flowing down from the stripping section. This completely or partly vaporized liquid stream is recirculated in its entirety or in part to the transesterification column. In the case of an embodiment without a stripping section, the liquid running down from the reaction zone is completely or partly vaporized, if appropriate, in a bottom vaporizer which may be used and recirculated completely or partly to the transesterification column.

The enrichment section(s) can, in preferred embodiments, be accommodated together with the reaction section(s) and, if appropriate, at least one stripping section in the transesterification column. Here, the gaseous mixture travelling upwards from the reaction zone(s) is introduced into a lower section of the enrichment section or, if appropriate, the lower enrichment section, with depletion in the alkylene carbonate or alkylene glycol taking place.

Below the reaction zone and any stripping section present, a mixture containing alkylene glycol, excess or unreacted alkylene carbonate, alkyl alcohol, dialkyl carbonate, transesterification catalysts and high-boiling compounds which are formed in the reaction or were originally present in the starting materials is obtained. When a stripping section is used, the content of low-boiling compounds, for example dialkyl carbonate and alcohol, is reduced, with further dialkyl carbonate and alkylene glycol sometimes being formed in the presence of the transesterification catalyst. The energy required for this is preferably supplied by one or more vaporizers.

In all sections of the transesterification column, i.e. both in the enrichment section and any stripping section and also in the reaction zone, it is possible to use random packing elements or ordered packing. The random packing elements or ordered packing to be used are those customary for distillations, as are described, for example, in Ullmann's Encyclopädie der Technischen Chemie, 4th edition, vol. 2, p. 528 ff. Examples of random packing elements are Raschig or Pall and Novalox rings, Berl, Intalex or Torus saddles, Interpack bodies and examples of ordered packings are sheet metal and mesh packings (e.g. BX packings, Montz Pak, Mellapak, Melladur, Kerapak and CY packing) made of various materials such as glass, stoneware, porcelain, stainless steel, plastic. Preference is given to random packing elements and ordered packings which have a large surface area, can be wetted readily and have a sufficient residence time of the liquid phase. These are, for example, Pall and Novolax rings, Berl saddles, BX packings, Montz Pak, Mellpak, Melladur, Kerapak and CY packings.

As an alternative, column trays such as sieve trays, bubble-cap trays, valve trays and tunnel trays are also suitable. In the reaction zone(s) of the transesterification column, column trays having long residence times with good mass transfer, for example bubblecap trays, valve trays or tunnel trays with high overflow weirs, are particularly preferred. The number of theoretical plates in the reaction zone is preferably from 3 to 50, particularly preferably from 10 to 50 and very particularly preferably from 10 to 40. The liquid hold-up is preferably from 1 to 80%, particularly preferably from 5 to 70% and very particularly preferably from 7 to 60%, of the interior column volume of the reaction zone. The more precise design of the reaction zone(s), any stripping section to be used and the enrichment section(s) can be carried out by a person skilled in the art.

The temperature of the reaction zone(s) is preferably in the range from 20 to 200° C., particularly preferably from 40 to 180° C., very particularly preferably from 50 to 160° C. It is advantageous to carry out the transesterification not only at atmospheric pressure but also at elevated or reduced pressure. The pressure of the reaction zone is therefore preferably in the range from 0.2 to 20 bar, particularly preferably from 0.3 to 10 bar, very particularly preferably from 0.4 to 5 bar. In the pressures indicated above and below are, unless explicitly stated otherwise, absolute pressures.

The vapour mixture containing dialkyl carbonate and alkyl alcohol which is taken off at the top of the transesterification column in the process for preparing the dialkyl carbonate is preferably, after condensation at the top of the transesterification column, passed in its entirety or in part to at least one further process step comprising at least one distillation column for the separation of dialkyl carbonate and alkyl alcohol.

The separation of the dialkyl carbonate and the alkyl alcohol is preferably effected by distillation in one or more distillation columns or in a combination of distillation and membrane separation, hereinafter referred to as hybrid process (see, for example, U.S. Pat. No. 4,162,200 A, EP 581 115 B1, EP 592 883 B1 and WO 2007/096343A1).

If alkyl alcohol and dialkyl carbonate form an azeotrope (e.g. methanol and dimethyl carbonate) it is also possible to use a two-stage process such as a dual pressure process, an extractive distillation, a heteroazeotropic distillation using a low-boiling entrainer or a hybrid process. The dual pressure process or a hybrid process is particularly preferably employed.

The separation of the dialkyl carbonate and the alkyl alcohol is very particularly preferably, even when the dialkyl carbonate and the alkyl alcohol form an azeotrope, carried out in a single distillation column. This distillation column is operated at a pressure which is higher than the pressure of the transesterification column(s). The operating pressure of the distillation column is in the range from 1 to 50 bar, preferably from 2 to 20 bar. Virtually pure dialkyl carbonate is taken off at the bottom of the distillation column and a mixture of dialkyl carbonate and alkyl alcohol is taken off at the top. All or part of this mixture is fed to the transesterification column (s). If the process for preparing dialkyl carbonate is coupled with a process for preparing diaryl carbonate formed by transesterification of said dialkyl carbonate with an aromatic hydroxyl compound, part of the mixture of dialkyl carbonate and alkyl alcohol which is taken off at the top of the distillation column can be passed to an appropriate work-up step for alkyl alcohol and dialkyl carbonate in the process stage for preparing diaryl carbonate.

In a particularly preferred embodiment when the dialkyl carbonate and the alkyl alcohol form an azeotrope, this work-up step is a dual pressure process. Such processes are known in principle to those skilled in the art (c.f., for example, Ullmann's Encyclopedia of Industrial Chemistry, Vol. 7, 2007, chapters 6.4 and 6.5; Chemie Ingenieur Technik (67) 11/95).

If alkyl alcohol and dialkyl carbonate form an azeotrope, the distillate from a first distillation column in the process step for the separation of dialkyl carbonate and alkyl alcohol preferably has a virtually azeotropic composition. In this case, this is preferably, in a dual pressure process, fed to at least one further distillation column which operates at an operating pressure which is below that of the first distillation column. Due to the different operating pressure, the position of the azeotrope shifts to smaller proportions of alkyl alcohol. The bottom product obtained from this second or further distillation column(s) is alkyl alcohol having a purity of from 90 to 100% by weight, based on the total weight of the bottom product isolated, and the distillate obtained is a virtually azeotropic mixture. The second or further distillation column (s) operating at a lower operating pressure is, in very particularly preferred embodiments, preferably operated using the heat of condensation from the overhead condenser(s) of the first distillation column.

In the dual pressure process, the pressure dependence of the azeotropic composition of a two-component mixture is utilized. In the case of a mixture of alkyl alcohol and dialkyl carbonate, for example methanol and dimethyl carbonate, the azeotropic composition shifts to higher alkyl alcohol contents with increasing pressure. If a mixture of these two components in which the alkyl alcohol content is below the azeotropic composition corresponding to the operating pressure of a column is fed to this column (dialkyl carbonate column), a mixture having a virtually azeotropic composition is thus obtained as distillate and virtually pure dialkyl carbonate is obtained as bottom product. The azeotropic mixture obtained in this way is fed to a further distillation column (alkyl alcohol column). This operates as a lower operating pressure than the dialkyl carbonate column. As a result, the position of the azeotrope is shifted to lower alkyl alcohol contents. This makes it possible to separate the azeotropic mixture obtained in the dialkyl carbonate column into a distillate having a virtually azeotropic composition and virtually pure alkyl alcohol. The distillate from the alkyl alcohol column is returned to the dialkyl carbonate column at a suitable point.

The operating pressure of the alkyl alcohol column is preferably selected so that the column can be operated using the waste heat from the dialkyl carbonate column. The operating pressure is in the range from 0.1 to 1 bar, preferably from 0.3 to 1 bar. The operating pressure of the dialkyl carbonate column is in the range from 1 to 50 bar, preferably from 2 to 20 bar.

An illustrative reaction flow diagram for the separation of dialkyl carbonate and alkyl alcohol by the dual pressure process is shown in FIG. 1.

A further preferred process for the separation of azeotropes of alkyl alcohol and dialkyl carbonate is the hybrid process. In the hybrid process, the separation of a two-component mixture is effected by means of a combination of distillation and membrane processes. Here, use is made of the fact that the components can be at least partly separated from one another by means of membranes because of their polar properties and their different molecular weight. In the case of a mixture of alkyl alcohol and dialkyl carbonate, for example methanol and dimethyl carbonate, use of suitable membranes gives, by means of pervaporation or vapour permeation, an alkyl alcohol-rich mixture as permeate and an alkyl alcohol-depleted mixture as retentate. If a mixture of these two components in which the alkyl alcohol content is below the azeotropic composition corresponding to the operating pressure of a column (dialkyl carbonate column) is fed to this column, a mixture having a significantly increased alkyl alcohol content compared to the feed is thus obtained as distillate and virtually pure dialkyl carbonate is obtained as bottom product.

In the case of a hybrid process made up of distillation and vapour permeation, the distillate is taken off in vapour form from the column. The gaseous mixture obtained in this way is, if appropriate after superheating, fed to a vapour permeation. This is operated in such a way that virtually the operating pressure of the column is set on the retentate side and a lower pressure is set on the permeate side. The operating pressure of the column is in the range from 1 to 50 bar, preferably from 1 to 20 bar and particularly preferably from 2 to 10 bar. The pressure on the permeate side is in the range from 0.05 to 2 bar. This gives an alkyl alcohol-rich fraction having an alkyl alcohol content of at least 70% by weight, preferably at least 90% by weight, based on the total weight of the fraction, on the permeate side. The retentate, which has a reduced alkyl alcohol content compared to the distillate from the column, is condensed if appropriate and fed back to the distillation column.

In the case of a hybrid process made up of distillation and pervaporation, the distillate from the column is taken off in liquid form. The mixture obtained in this way is, if appropriate, after superheating, fed to a pervaporation. This is operated so that an operating pressure which is identical to or above that in the column is set on the retentate side and a lower pressure is set on the permeate side. The operating pressure of the column is in the range from 1 to 50 bar, preferably from 1 to 20 bar and particularly preferably from 2 to 10 bar. The pressure on the permeate side is in the range from 0.05 to 2 bar. This gives an alkyl alcohol-rich gaseous fraction having an alkyl alcohol content of at least 70% by weight, preferably at least 90% by weight, based on the total weight of the fraction, on the permeate side. The liquid retentate, which has an alkyl alcohol content lower than that in the distillate from the column, is fed back to the distillation column. The vaporization of the permeate requires heat which may not be present in sufficient quantity in the feed stream to the pervaporation. A membrane separation by means of pervaporation can therefore be heated, if necessary, by means of additional heat exchangers which are either integrated or, if appropriate, installed between a plurality of pervaporation steps connected in series.

The separation of dialkyl carbonate and alkyl alcohol is in the case of a hybrid process particularly preferably carried out by means of a combination of distillation and vapour permeation.

The heat required for the separation of alkyl alcohol and dialkyl carbonate is supplied at a temperature in the range from 100° C. to 300° C., preferably from 100° C. to 230° C. and particularly preferably from 120° C. to 200° C.

The distillation column(s) for purifying the dialkyl carbonate preferably has/have an enrichment section which preferably has from 5 to 40 theoretical plates for concentrating the alkyl alcohol and a stripping section which preferably has from 5 to 40 theoretical plates for concentrating the dialkyl carbonate.

The process for preparing dialkyl carbonate is preferably carried out continuously.

All the references described above are incorporated by reference in their entireties for all useful purposes.

While there is shown and described certain specific structures embodying the invention, it will be manifest to those skilled in the art that various modifications and rearrangements of the parts may be made without departing from the spirit and scope of the underlying inventive concept and that the same is not limited to the particular forms herein shown and described.

In the figures, the symbols/numerals have the following meanings:

K1 transesterification column
K2 first distillation column for the separation of the mixture containing dialkyl carbonate and alkyl alcohol
K3 second distillation column for the separation of the mixture comprising dialkyl carbonate and alkyl alcohol
1 feed stream containing alkylene carbonate and/or optionally catalyst
2 feed stream containing virtually pure alkyl alcohol
3 feed stream containing alkyl alcohol and dialkyl carbonate
4 stream containing alkylene glycol
5 stream containing purified dialkyl carbonate
6 stream containing dialkyl carbonate and alkyl alcohol
7 stream containing virtually pure alkyl alcohol
8 stream containing extractant (preferably alkylene carbonate)
9 stream containing extractant (preferably alkylene carbonate)
10 stream containing extractant (preferably alkylene carbonate)
i. heat exchanger for preheating the feed to the distillation column for purifying the dialkyl carbonate, with the heat of condensation liberated at the top of this distillation column being used for preheating
ii heat exchanger for preheating the feed to the distillation column for purifying the dialkyl carbonate, with heat being withdrawn from the bottoms containing virtually pure dialkyl carbonate
a intermediate heater FIG. 1 describes a transesterification step for alkylene carbonate and alkyl alcohol by means of reactive rectification in a first transesterification column (K1) in general and the work-up of the mixture containing dialkyl carbonate and alkyl alcohol which is obtained at the top of the transesterification column by means of dual pressure distillation in a first distillation column (K2) and a second distillation column (K3) with an intermediate heater (a) in the transesterification column.

Figure 2:
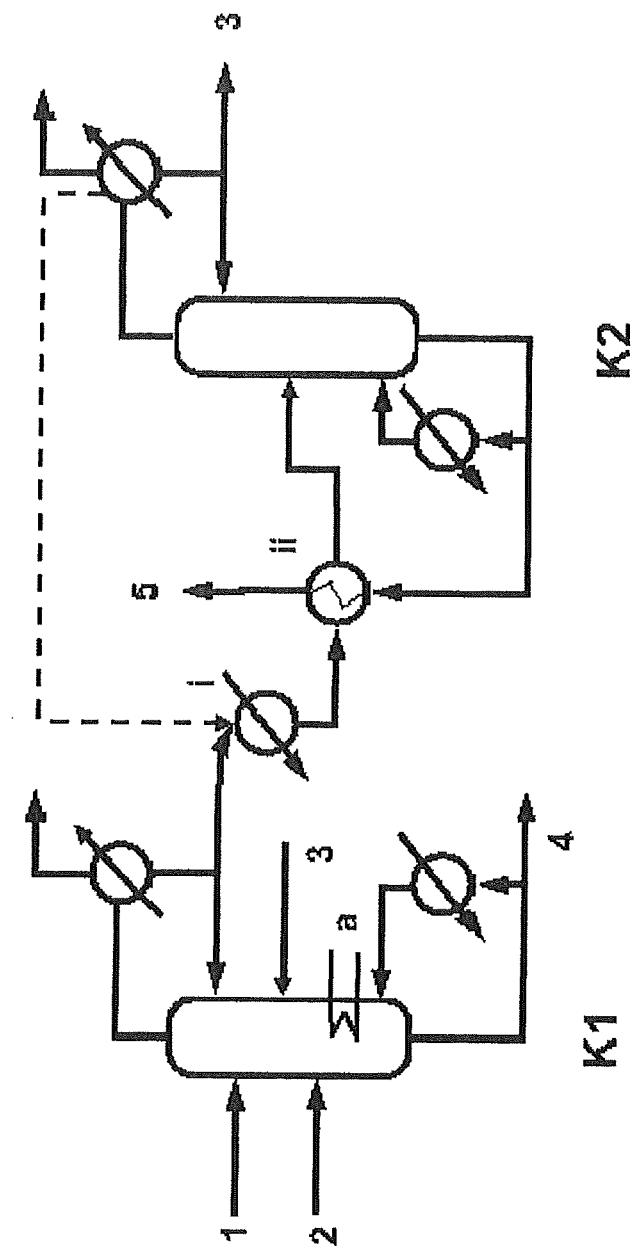
FIG. 2 depicts a process for preparing dialkyl carbonates according to another embodiment of the present invention.

FIG. 2 describes a transesterification step for alkylene carbonate and alkyl alcohol by means of reactive rectification in a first transesterification column (K1) containing an intermediate heater (a) in general and the work-up of the mixture containing dialkyl carbonate and alkyl alcohol which is obtained at the top of the transesterification column by means of a single distillation column (K2).

Figure 3:
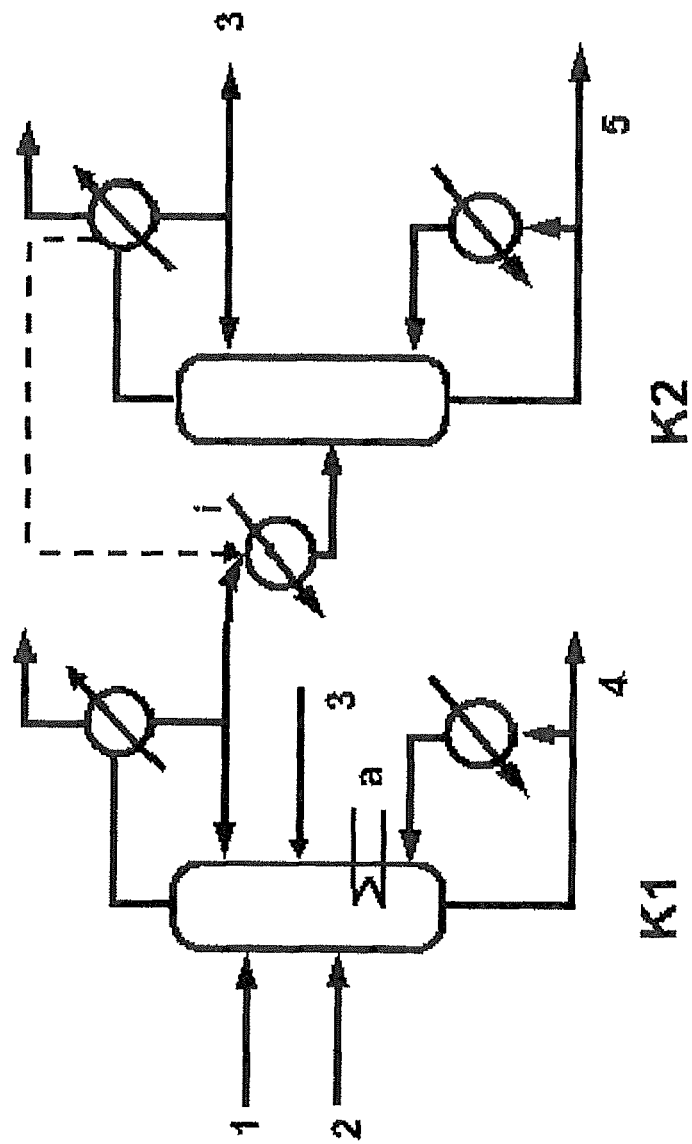
FIG. 3 depicts a process for preparing dialkyl carbonates according to another embodiment of the present invention.
Figure 4:
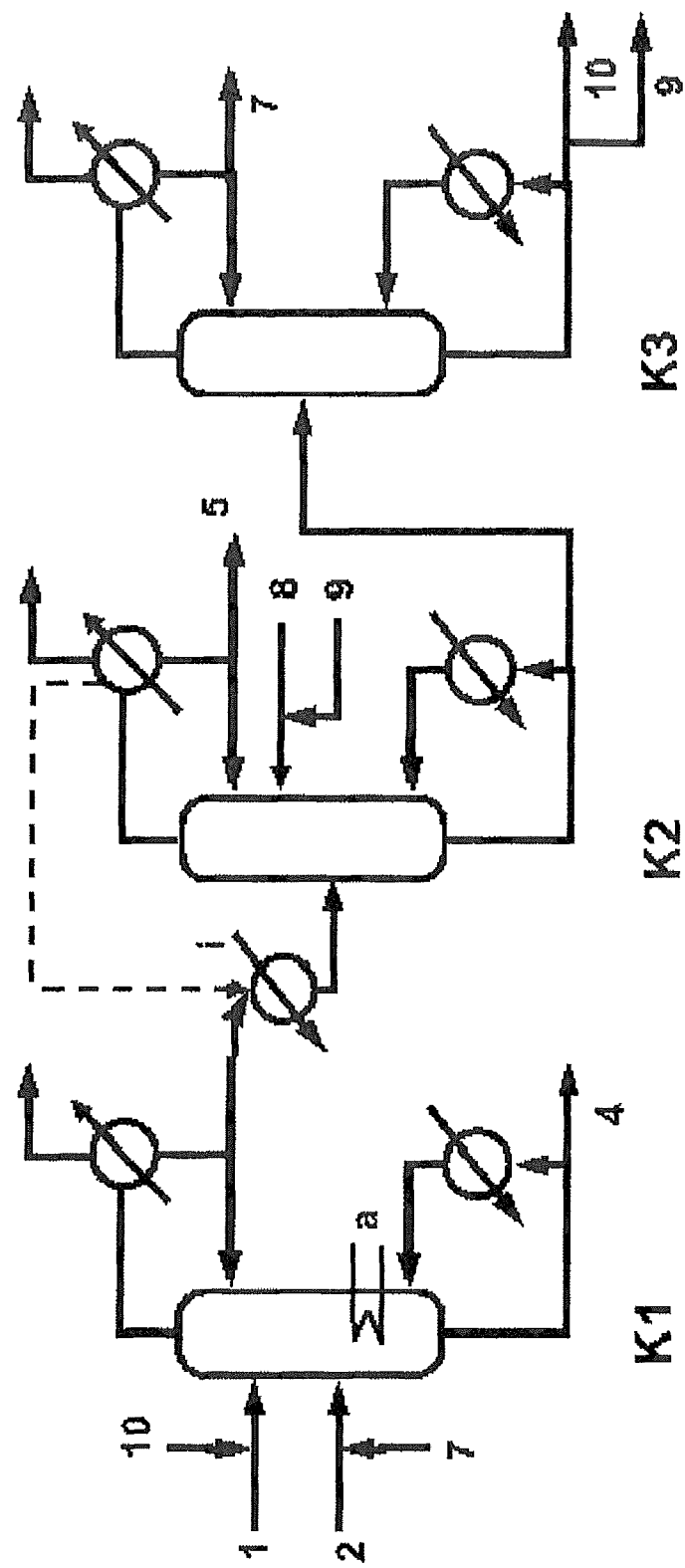
FIG. 4 depicts a process for preparing dialkyl carbonates according to another embodiment of the present invention.

FIG. 3 is like FIG. 2 but without preheating of the feed to the distillation column (K2) by means of the bottoms therefrom FIG. 4 describes a transesterification step for alkylene carbonate and alkyl alcohol by means of reactive rectification in a first transesterification column (K1) containing an intermediate heater (a) in general and the work-up of the mixture containing dialkyl carbonate and alkyl alcohol which is obtained at the top of the transesterification column by means of extractive distillation in a first distillation column (K2) and a second distillation column (K3), with the alkylene carbonate preferably being used as extractant.

Figure 5:
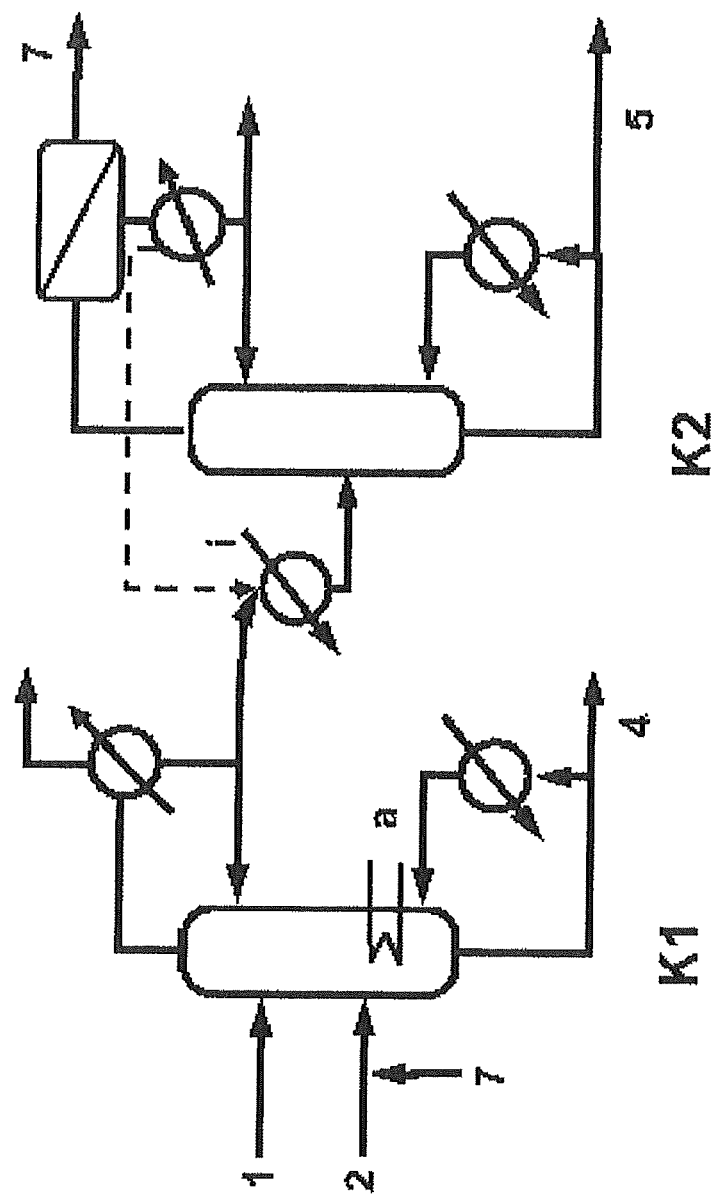
FIG. 5 depicts a process for preparing dialkyl carbonates according to another embodiment of the present invention.

FIG. 5 describes a transesterification step for alkylene carbonate and alkyl alcohol by means of reactive rectification in a first transesterification column (K1) containing an intermediate heater (a) in general and the work-up of the mixture containing dialkyl carbonate and alkyl alcohol which is obtained at the top of the transesterification column by means of distillation and vapour permeation in a distillation column (K2).

Figure 6:
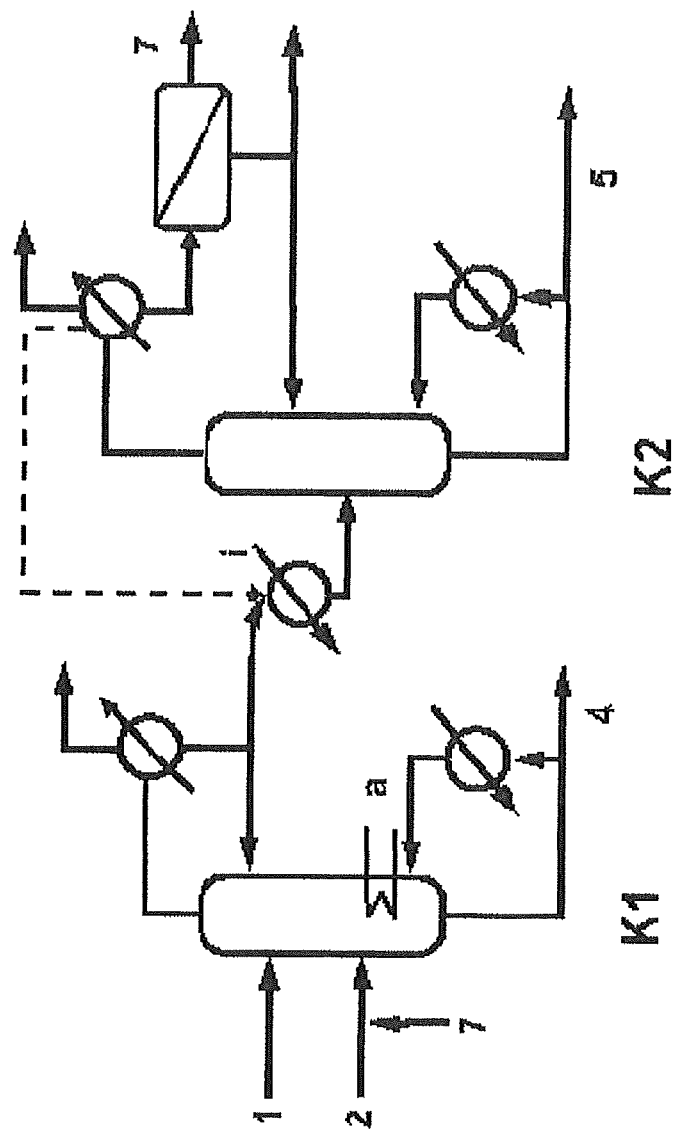
FIG. 6 depicts a process for preparing dialkyl carbonates according to another embodiment of the present invention.

FIG. 6 describes a transesterification step for alkylene carbonate and alkyl alcohol by means of reactive rectification in a first transesterification column (K1) containing an intermediate heater (a) in general and the work-up of the mixture containing dialkyl carbonate and alkyl alcohol which is obtained at the top of the transesterification column by means of distillation and pervaporation in a distillation column (K2).

EXAMPLES

The preferred mode of operation for the process of the invention will now be indicated in detail with the aid of an example. Example 1 shows the preferred mode of operation for the transesterification column. This example should not be interpreted as limiting the invention in any way.

The advantage of the present invention, namely the reduction in the consumption of fresh heating steam while maintaining the high product quality, by installation of a technical device for intermediate heating, compared to other methods of operation without the abovementioned intermediate heater or in the case of less favourable positioning of the intermediate heater is shown in the comparative examples.

Example 1 (According to the Invention)

This example uses the reference numerals of FIG. 2. A reactive distillation column comprising an enrichment section having 9 theoretical plates, a reaction zone having 25 reaction trays (holdup/tray: 0.6 m$^3$) and a stripping section having 4 theoretical plates is operated at a pressure at the top of the column of 400 mbar (absolute) and a reflux ratio of 0.66.

9000 kg/h of ethylene carbonate and 175 kg/h of a mixture of 33.3% by weight of KOH and 66.7% by weight of ethylene glycol (stream 1) are fed continuously into the upper column region directly above the first reaction tray. Between the 8$^{th}$ and 9$^{th}$ reaction trays, 21 371 kg/h of a gaseous mixture (stream 3) of 83.7% by weight of methanol and 16.3% by weight of dimethyl carbonate are fed in. In addition, 7123 kg/h of a gaseous mixture (stream 2) of 99.5% by weight of methanol, 0.41% by weight of ethylene glycol and 672 ppm of dimethyl carbonate are fed in at the lower end of the reaction zone.

A partial condenser condenses the vapour stream at the top of the column (K1) at 40° C. 6 kg/h of gaseous distillate and also 30 644 kg/h of liquid distillate having a composition of 59% by weight of methanol and 41% by weight of dimethyl carbonate, which is passed to dimethyl carbonate purification column, are obtained.

A device for intermediate heating (heat exchanger a) which has a heating power of 2000 kW and is operated by means of steam at a pressure level of 1.5 bar as heating medium is installed in the stripping section directly above the bottom vaporizer of the transesterification column (K1).

This gives 7019 kg/h of liquid bottom product (stream 4) which comprises mainly ethylene glycol and, inter alia, 477 ppm of ethylene carbonate. The bottom vaporizer is operated by means of heating steam at a pressure level of 3 bar at 102° C.

The subsequent dialkyl carbonate purification column (K2) comprises an enrichment section having 28 theoretical plates and a stripping section having 11 theoretical plates and is operated at a pressure of 10 bar (absolute) at the top of the column and a reflux ratio of 1.0. The 30 644 kg/h of the distillate from the transesterification column, which contains 59% by weight of methanol and 41% by weight of dimethyl carbonate, is fed continuously into the lower region of the column between the 27th and 28th theoretical separating plate.

A partial condenser condenses the vapour stream at the top of the column (K2) at 137° C. This gives both 21 kg/h of gaseous distillate and 21 378 kg/h of liquid distillate (stream 3) having a composition of 84% by weight of methanol and 16% by weight of dimethyl carbonate. Here, 10 000 kW of heating power, which can be utilized for the generation of steam at a pressure level of 1.5 bar, is removed.

This gives 9245 kg/h of liquid bottom product (stream 5) having a composition of 99.5% by weight of dimethyl carbonate and 0.5% by weight of methanol. The bottom vaporizer is operated by means of heating steam at a pressure level of 16 bar at 183° C. and has a heating power of 10 396 kW. Part of the vapour obtained at the top of the dialkyl carbonate purification column can be utilized, inter alia, for preheating of the feed to this column and for vaporization of the feed stream (3) to the transesterification column (K1). 2000 kW of steam energy are used for the intermediate heater of the transesterification column.

As a result of the use of 2000 kW of the energy of condensation recovered at the top of the dialkyl carbonate purification column in the intermediate heater of the transesterification column, only a heating power of 939 kW, which is supplied as heating steam at a pressure level of 3 bar, is required for operating the bottom vaporizer in the transesterification column.

Example 2 (Comparative)

The same reactive distillation column (K1) and the same dialkyl carbonate purification column (K2) as described in Example 1 according to the invention is used. The transesterification column (K1) is operated at a pressure at the top of the column of 400 mbar (absolute) and a reflux ratio of 0.66.

9000 kg/h of ethylene carbonate and 175 kg/h of a mixture of 33.3% by weight of KOH and 66.7% by weight of ethylene glycol are fed continuously into the upper column region directly above the first reaction tray. Between the 8$^{th}$ and 9$^{th}$ reaction trays, 21 371 kg/h of a gaseous mixture of 83.7% by weight of methanol and 16.3% by weight of dimethyl carbonate are fed in. In addition, 7123 kg/h of a gaseous mixture of 99.5% by weight of methanol, 0.41% by weight of ethylene glycol and 672 ppm of dimethyl carbonate are fed in at the lower end of the reaction zone. The ratio of the total methanol fed in and the ethylene carbonate remains the same as in Example 1.

A partial condenser condenses the vapour stream at the top of the column at 40° C. 6 kg/h of gaseous distillate and also 30 644 kg/h of liquid distillate having a composition of 59% by weight of methanol and 41% by weight of dimethyl carbonate, which is passed to further purification steps, are obtained.

The intermediate heater (a) is not in operation.

This then gives 7019 kg/h of liquid bottom product (stream 4) from the transesterification column (K1), which comprises mainly ethylene glycol and, inter alia, 468 ppm of ethylene carbonate. The bottom vaporizer of the transesterification column is operated by means of heating steam at a pressure level of 3 bar at 102° C. and then requires a heating power of 2939 kW, hence a heating power which is 2000 kW higher than in the example according to the invention.

Example 3 (Comparative)

The same reactive distillation column (K1) and the same dialkyl carbonate purification column (K2) as described in Example 1 according to the invention is used. The transesterification column (K1) is operated at a pressure at the top of the column of 400 mbar (absolute) and a reflux ratio of 0.66.

9000 kg/h of ethylene carbonate and 175 kg/h of a mixture of 33.3% by weight of KOH and 66.7% by weight of ethylene glycol are fed continuously into the upper column region directly above the first reaction tray. Between the 8$^{th}$ and 9$^{th}$ reaction trays, 21 371 kg/h of a gaseous mixture of 83.7% by weight of methanol and 16.3% by weight of dimethyl carbonate are fed in. In addition, 7123 kg/h of a gaseous mixture of 99.5% by weight of methanol, 0.41% by weight of ethylene glycol and 672 ppm of dimethyl carbonate are fed in at the lower end of the reaction zone.

A partial condenser condenses the vapour stream at the top of the column at 40° C. 6 kg/h of gaseous distillate and also 30 644 kg/h of liquid distillate having a composition of 59% by weight of methanol and 41% by weight of dimethyl carbonate, which is passed to further purification steps, are obtained.

A device for the intermediate heating which has a heating power of 2000 kW and is operated by means of steam at a pressure level of 1.5 bar as heating medium is installed at the 20th reaction tray of the column.

This then gives 7019 kg/h of liquid bottom product comprising mainly ethylene glycol and, inter alia, 1% of ethylene carbonate. The bottom vaporizer is operated by means of heating steam at a pressure level of 3 bar at 102° C. and requires a heating power of 939 kW. The shift in position of the intermediate heater in the transesterification column leads to a drastic increase in the content of ethylene carbonate in the liquid bottom product (stream 4) form the transesterification column (K1).

The invention claimed is:

1. A process for preparing dialkyl carbonate from cyclic alkylene carbonate and alkyl alcohol in at least one transesterification column and at least one subsequent distillation column for purifying the dialkyl carbonate formed in the transesterification column, wherein the at least one transesterification column comprises comprises at least one reaction zone and at least one enrichment section arranged above the reaction zone, and wherein the column comprises at least one enrichment section in the upper part of the column and at least one stripping section in the lower part of the column, wherein the process comprises heating a liquid stream in the at least one transesterification column with a technical device arranged above a bottom vaporizer of the at least one transesterification column, wherein the technical device uses a medium for heating the internal liquid stream in the column at a temperature ($T_I$) which is less than the temperature $T_{BV}$ of the medium used in the bottom vaporizer, recovering, partly or entirely, the energy of the medium for heating the internal liquid stream in the column from another chemical production process, and, wherein the at least one transesterification column comprises a stripping section arranged below the reaction zone and the technical device for heating the internal liquid stream in the column is arranged in the stripping section.

2. The process according to claim 1, wherein the energy at the temperature level $T_I$ is made available, in its entirety or in part, directly or indirectly by condensation as heat of condensation.

3. The process according to claim 1 wherein the transesterification is carried out in countercurrent in at least one transesterification column in the presence of a catalyst in such a way that alkylene carbonate is introduced into the upper part of the column and a dialkyl carbonate-containing alkyl alcohol having a dialkyl carbonate content of from 0.2 to 30% by weight is introduced into the middle or lower part of the reaction zone of the at least one transesterification column.

4. The process according to claim 3, wherein a further stream comprising virtually pure alkyl alcohol is fed into the at least one transesterification column at a point of introduction arranged below the point of introduction of the dialkyl carbonate-containing alkyl alcohol stream.

5. The process according to claim 4, wherein the energy of the medium is recovered at the temperature level $T_I$ in the condensation of the mixture at the top of the at least one distillation column for purifying the dialkyl carbonate.

6. The process according to claim 2 wherein the transesterification is carried out in countercurrent in at least one transesterification column in the presence of a catalyst in such a way that alkylene carbonate is introduced into the upper part of the column and a dialkyl carbonate-containing alkyl alcohol having a dialkyl carbonate content of from 0.2 to 30% by weight is introduced into the middle or lower part of the reaction zone of the at least one transesterification column.

* * * * *